United States Patent
Zalipsky et al.

[11] Patent Number: 6,051,251
[45] Date of Patent: Apr. 18, 2000

[54] LIPOSOME LOADING METHOD USING A BORONIC ACID COMPOUND

[75] Inventors: Samuel Zalipsky, Redwood City; Paul S. Uster, Tracy; George Z. Zhu, San Jose, all of Calif.

[73] Assignee: Alza Corporation, Palo Alto, Calif.

[21] Appl. No.: 09/196,425

[22] Filed: Nov. 19, 1998

Related U.S. Application Data

[60] Provisional application No. 60/066,230, Nov. 20, 1997.

[51] Int. Cl.[7] ..................................... A61K 9/127
[52] U.S. Cl. .............................. 424/450; 264/4.1; 264/4.3
[58] Field of Search ................... 424/450, 1.21, 424/9.34, 9.51, 417, 94.3, 812; 436/829; 935/54; 264/4.1, 4.3

[56] References Cited

U.S. PATENT DOCUMENTS

| | | | |
|---|---|---|---|
| 5,688,928 | 11/1997 | Stolowitz | 530/391.1 |
| 5,831,045 | 11/1998 | Stolowitz | 536/22.1 |
| 5,852,178 | 12/1998 | Stolowitz | 530/402 |

*Primary Examiner*—Gollamudi S. Kishore
*Attorney, Agent, or Firm*—Judy M. Mohr; Dehlinger & Associates

[57] ABSTRACT

A method for loading a therapeutic compound having a cis diol moiety into pre-formed liposomes is described. The method includes adding to a suspension of liposomes (i) the compound to be loaded into the liposomes and (ii) a boronic acid compound, thereby achieving accumulation of the compound within the liposomes.

21 Claims, 6 Drawing Sheets

LIPOSOME LOADING METHOD USING A BORONIC ACID COMPOUND

This application claims the priority of provisional application Ser. No. 60/066,230, filed Nov. 20, 1997, and which is incorporated herein by reference.

FIELD OF THE INVENTION

The present invention relates to a method for loading a therapeutic compound into preformed liposomes using a boronic acid compound as a shuttle.

BACKGROUND OF THE INVENTION

Liposomes serve as carriers for a variety of therapeutic agents and drug delivery systems utilizing liposomes offer the potential of improved delivery properties, including enhanced blood circulation time, reduced cytotoxicity, sustained drug release, and targeting to selected tissues.

In utilizing liposomes for drug delivery, it is generally desirable to load the liposomes to high encapsulated drug concentration. Rate of leakage of the drug from the liposomes should also be low, to preserve the advantages of drug delivery in liposome-entrapped form.

A variety of drug-loading methods are available for preparing liposomes with entrapped drug. In the case of many lipophilic drugs, efficient drug entrapment can be achieved by preparing a mixture of vesicle-forming lipids and the drug, e.g., in a dried film, and hydrating the mixture to form liposomes with drug entrapped predominantly in the lipid bilayer phase of the vesicles. Assuming the partition coefficient of the drug favors the lipid phase, high loading efficiency and stable drug retention can be achieved.

The same type of passive loading may also be employed for preparing liposomes with encapsulated hydrophilic compounds. In this case, the drug is usually dissolved in the aqueous medium used to hydrate a lipid film of vesicle-forming lipids.

Depending on the hydration conditions, and the nature of the drug, encapsulation efficiencies of between about 5-20%; are typically obtained, with the remainder of the drug being in the bulk aqueous phase. An additional processing step for removing non-encapsulated drug is usually required.

A more efficient method for encapsulated hydrophilic drugs, involving reverse evaporation from an organic solvent, has also been reported (Szoka, F., et al., *Ann. Rev. Biophys. Bioeng.* 9:467 (1980)). In this approach, a mixture of hydrophilic drug and vesicle-forming lipids are emulsified in a water-in-oil emulsion, followed by solvent removal to form an unstable lipid-monolayer gel. When the gel is agitated, typically in the presence of added aqueous phase, the gel collapses to form oligolamellar liposomes with high (up to 50%) encapsulation of the drug.

In the case of ionizable hydrophilic or amphipathic drugs, even greater drug-loading efficiency can be achieved by loading the drug into liposomes against a transmembrane ion gradient (Nichols, J. W., et al., *Biochim. Biophys. Acta* 455:269–271 (1976); Cramer, J., et al., *Biochemical and Biophysical Research Communications* 75 (2): 295–301 (1977)). This loading method, generally referred to as remote loading, typically involves a drug having an ionizable amine group which is loaded by adding it to a suspension of liposomes prepared to have a lower inside/higher outside ion gradient, often a pH gradient.

However, drugs suitable for loading by remote loading procedures must be sufficiently lipophilic to pass through the liposome lipid bilayer during the loading process. For some remote loading procedures, such as remote loading under an ammonium sulfate gradient, the drug to be loaded must also have an ionizable amine group. Necessary features such as these limit the number of drugs for which remote loading processes described to date are useful.

SUMMARY OF THE INVENTION

Accordingly, it is an object of the invention to provide a liposome loading procedure for drugs which in their native form are insufficiently lipophilic for remote loading.

It is a further object of the invention to provide a method for loading a lipophobic therapeutic compound into preformed liposomes.

It is a further object of the invention to provide a method for loading a therapeutic compound having two nearby hydroxyl groups into preformed liposomes.

In one aspect, the invention includes a method for loading a therapeutic compound having a cis diol moiety into liposomes, comprising adding to a suspension of liposomes (i) the compound to be loaded into the liposomes and (ii) a boronic acid compound, where the adding is effective to achieve accumulation of the compound within the liposomes.

In one embodiment of the method, the boronic acid compound added is selected from phenylboronic acid, 2-pyridylboronic acid, 3-aminophenylboronic acid, p-tolueneboronic acid, 3,5-bis(trifluoromethyl)benzeneboronic acid, 4-carboxybenzeneboronic acid, 3-nitrobenzene boronic acid and 4-methylbenzeneboronic acid.

In one preferred embodiment, between 2–50 mM of the boronic acid compound is added, and in a preferred embodiment between 2–50 mM of phenylboronic acid is employed.

In another embodiment, the method includes a compound having a 1,2 cis-diol moiety. In another embodiment, a compound having a 1,3 cis-diol moiety is added.

In other embodiments, a glycoside compound is added for loading into the liposomes, or a compound selected from the group consisting of galactosamine, ribavirin, idoxuridine, amikacin, tobramycin, and glucosamine is added.

The liposomes in the suspension, in one embodiment, each have a surface coating of hydrophilic polymer chains.

In another aspect, the invention includes a method for loading a therapeutic compound having a cis diol group into liposomes, comprising preparing a suspension of liposomes composed of a vesicle-forming lipid and incubating the liposomes in the presence of (i) the compound to be loaded and (ii) a boronic acid compound. The incubation is effective to achieve accumulation of the compound within the liposomes.

In one embodiment of this aspect, the liposomes are prepared to have an inside/outside ion gradient for use in loading an ionizable therapeutic compound. In one preferred embodiment, the liposomes have an inside/outside ammonium ion gradient and the compound to be loaded has an ionizable amine.

In another embodiment, the method includes the further step of removing the boronic acid after the incubating step.

These and other objects and features of the invention will be more fully appreciated when the following detailed description of the invention is read in conjunction with the accompanying drawings.

DETAILED DESCRIPTION OF THE INVENTION

I. Definitions

Figure 1A:
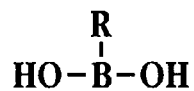
FIGS. 1A–1E show structures for a general boronic acid compound (FIG. 1A), and for phenylboronic acid (FIG. 1B), 2-pyridylboronic acid (FIG. 1C), 3-aminophenylboronic acid (FIG. 1D) and p-tolueneboronic acid (FIG. 1E)

"Boronic acid compound" as used herein refers to a compound of the form $R-B-(OH)_2$, where R is hydrogen or is an alkyl moiety or aryl moiety, including aryl heterocycles and aryl moieties which are substituted, for example with alkoxy, hydroxyl, alkyl or amine substitutions. The boronic acid compound should preferably be pharmaceutically acceptable for use in vivo.

"Glycoside" refers to any substance with an alcohol component in which a glycosyl group has replaced the hydrogen in the hydroxyl group.

II. Liposome Loading Method

In one aspect the invention includes a method of loading a therapeutic compound having two nearby hydroxyl groups, e.g., a diol moiety and preferably a 1,2 or 1,3 cis diol moiety, into preformed liposomes. As will be described below, the diol-containing compound is transported into the liposome by a boronic acid compound, which forms a transiently stable complex with the compound. Before describing the loading method, the liposome components will be described.

A. Liposome Components and Preparation

The liposomes of the invention are composed of vesicle-forming lipids, generally including amphipathic lipids having both hydrophobic tail groups and polar head groups. A characteristic of a vesicle-forming lipid is its ability to either (a) form spontaneously into bilayer vesicles in water, as exemplified by the phospholipids, or (b) be stably incorporated into lipid bilayers, by having the hydrophobic portion in contact with the interior, hydrophobic region of the bilayer membrane, and the polar head group oriented toward the exterior, polar surface of the membrane. A vesicle-forming lipid for use in the present invention is any conventional lipid possessing one of the characteristics described above.

The vesicle-forming lipids of this type are preferably those having two hydrocarbon tails or chains, typically acyl groups, and a polar head group. Included in this class are the phospholipids, such as phosphatidylcholine (PC), phosphatidylethanolamine (PE), phosphatidic acid (PA), phosphatidylglycerol (PG), and phosphatidylinositol (PI), where the two hydrocarbon chains are typically between about 14–22 carbon atoms in length, and have varying degrees of unsaturation. Preferred phospholipids include PE and PC. An exemplary PC is hydrogenated soy phosphatidylcholine (HSPC). Single chain lipids, such as sphingomyelin (SM) may also be used.

The above-described lipids and phospholipids whose acyl chains have a variety of degrees of saturation can be obtained commercially, or prepared according to published methods. Other lipids that can be included in the invention are glycolipids. The term "glycolipid" as used herein encompasses lipids having two hydrocarbon chains, one of which is the hydrocarbon chain of sphingosine, and one or more sugar residues.

Lipids for use in the present invention may be relatively "fluid" lipids, meaning that the lipid phase has a relatively low lipid melting temperature, e.g., at or below room temperature, or alternately, relatively "rigid" lipids, meaning that the lipid has a relatively high melting point, e.g., at temperatures up to 50° C. As a general rule, the more rigid, i.e., saturated lipids, contribute to greater membrane rigidity in the lipid bilayer structure, and thus to more stable drug retention after active drug loading. Preferred lipids of this type are those having phase transition temperatures above about 37° C.

The liposomes may additionally include lipids that can stabilize a vesicle or liposome composed predominantly of phospholipids. The most frequently employed lipid from this group is cholesterol at levels between 25 to 45 mole percent.

Liposomes used in the invention preferably contain between 30–75 percent phospholipids, preferably phosphatidylcholine (PC), 25–45 percent cholesterol. One exemplary liposome formulation contains 60 mole percent phosphatidylcholine and 40 mole percent cholesterol.

In one embodiment, the liposomes of the invention include a surface coating of a hydrophilic polymer chain. "Surface-coating" refers to the coating of any hydrophilic polymer on the surface of liposomes. The hydrophilic polymer is included in the liposome by including in the liposome composition one or more vesicle-forming lipids derivatized with a hydrophilic polymer chain. The vesicle-forming lipids which can be used are any of those described above for the first vesicle-forming lipid component, however, vesicle-forming lipids with diacyl chains, such as phospholipids, are preferred. One preferred phospholipid is phosphatidylethanolamine (PE), which contains a reactive amino group convenient for coupling to the activated polymers. One exemplary PE is distearyl PE (DSPE).

A preferred hydrophilic polymer for use in coupling to a vesicle forming lipid is polyethyleneglycol (PEG), preferably as a PEG chain having a molecular weight between 1,000–10,000 Daltons, more preferably between 1,000–5,000 Daltons, most preferably between 2,000–5,000 Daltons. Methoxy or ethoxy-capped analogues of PEG are also preferred hydrophilic polymers, commercially available in a variety of polymer sizes, e.g., 120–20,000 Daltons.

Other hydrophilic polymers which may be suitable include polylactic acid, polyglycolic acid, polyvinylpyrrolidone, polymethyloxazoline, polyethyloxazoline, polyhydroxypropyl methacrylamide, polymethacrylamide, polydimethylacrylamide, and derivatized celluloses, such as hydroxymethylcellulose or hydroxyethylcellulose.

Preparation of lipid-polymer conjugates containing these polymers attached to a suitable lipid, such as PE, have been described, for example in U.S. Pat. No. 5,395,619, which is expressly incorporated herein by reference, and by Zalipsky in STEALTH LIPOSOMES (1995). Typically, between about 1–20 mole percent of the polymer-derivatized lipid is included in the liposome-forming components during liposome formation.

The hydrophilic polymer chains provide a surface coating of hydrophilic chains sufficient to extend the blood circulation time of the liposomes in the absence of such a coating. The extent of enhancement of blood circulation time is severalfold over that achieved in the absence of the polymer coating, as described in co-owned U.S. Pat. No. 5,013,556, which is expressly incorporated herein by reference.

Further, the liposomes may be prepared to contain surface groups, such as antibodies or antibody fragments, small effector molecules for interacting with cell-surface receptors, antigens, and other like compounds for achieving desired target-binding properties to specific cell populations. Here the lipid component included in the liposomes would include either a lipid derivatized with the targeting molecule, or a lipid having a polar-head chemical group that can be derivatized with the targeting molecule in preformed liposomes, according to known methods.

The liposomes may be prepared by a variety of techniques, such as those detailed in Szoka, F., Jr., et al., Ann. Rev. Biophys. Bioeng. 9:467 (1980), and a specific example of liposomes prepared in support of the present invention is set forth in Example 1. Typically, the liposomes are multilamellar vesicles (MLVs), which can be formed by simple lipid-film hydration techniques. In this procedure, a mixture of liposome-forming lipids and including a vesicle-forming lipid derivatized with a hydrophilic polymer are dissolved in a suitable organic solvent which is evaporated in a vessel to form a dried thin film. The film is then covered by an aqueous medium to form MLVs, typically with sizes between about 0.1 to 10 microns. Exemplary methods of preparing derivatized lipids and of forming polymer-coated liposomes have been described in co-owned U.S. Pat. Nos. 5,013,556, 5,631,018 and 5,395,619, which are incorporated herein by reference.

After liposome formation, the vesicles may be sized to achieve a size distribution of liposomes within a selected range, according to known methods. The liposomes are preferably uniformly sized to a selected size range between 0.04 to 0.25 µm. Small unilamellar vesicles (SUVs), typically in the 0.04 to 0.08 µm range, can be prepared by extensive sonication or homogenization of the liposomes. Homogeneously sized liposomes having sizes in a selected range between about 0.08 to 0.4 microns can be produced, e.g., by extrusion through polycarbonate membranes or other defined pore size membranes having selected uniform pore sizes ranging from 0.03 to 0.5 microns, typically, 0.05, 0.08, 0.1, or 0.2 microns. The pore size of the membrane corresponds roughly to the largest size of liposomes produced by extrusion through that membrane, particularly where the preparation is extruded two or more times through the same membrane. The sizing is preferably carried out in the original lipid-hydrating buffer, so that the liposome interior spaces retain this medium throughout the initial liposome processing steps.

In one embodiment of the invention, the liposomes are prepared to include an ion gradient, such as a pH gradient or an amine gradient, across the liposome lipid bilayer. One method for preparing ion gradient liposomes is set forth in Example 1, where a mixture of liposome-forming lipids is dissolved in a suitable organic solvent and evaporated in a vessel to form a thin film. The film is then covered with an aqueous medium containing the solute species that will form the aqueous phase in the liposome interior spaces in the final liposome preparation. The lipid film hydrates to form multi-lamellar vesicles (MLVs), typically with heterogeneous sizes between about 0.1 to 10 microns. The liposome are then sized, as described above, to a uniform selected size range.

After sizing, the external medium of the liposomes is treated to produce an ion gradient across the liposome membrane, which is typically a lower inside/higher outside concentration gradient. This may be done in a variety of ways, e.g., by (i) diluting the external medium, (ii) dialysis against the desired final medium, (iii) molecular-sieve chromatography, e.g., using SEPHADEX G-50, against the desired medium, or (iv) high-speed centrifugation and resuspension of pelleted liposomes in the desired final medium.

The external medium which is selected will depend on the mechanism of gradient formation and the external pH desired, as will now be considered.

In the simplest approach for generating a pH gradient, the hydrated sized liposomes have a selected internal-medium pH. The suspension of the liposomes is titrated until a desired final pH is reached, or treated as above to exchange the external phase buffer with one having the desired external pH. For example, the original medium may have a pH of 5.5, in a selected buffer, e.g., glutamate or phosphate buffer, and the final external medium may have a pH of 8.5 in the same or different buffer. The internal and external media are preferably selected to contain about the same osmolarity, e.g., by suitable adjustment of the concentration of buffer, salt, or low molecular weight solute, such as sucrose.

In another more preferred approach, the proton gradient used for drug loading is produced by creating an ammonium ion gradient across the liposome membrane, as described, for example, in U.S. Pat. No. 5,192,549. Here the liposomes are prepared in an aqueous buffer containing an ammonium salt, typically 0.1 to 0.3 M ammonium salt, such as ammonium sulfate, at a suitable pH, e.g., 5.5 to 7.5. After liposome formation and sizing, the external medium is exchanged for one lacking ammonium ions, e.g., the same buffer but one in which ammonium sulfate is replaced by NaCl or a sugar that gives the same osmolarity inside and outside of the liposomes.

After liposome formation, the ammonium ions inside the liposomes are in equilibrium with ammonia and protons. Ammonia is able to penetrate the liposome bilayer and escape from the liposome interior. Escape of ammonia continuously shifts the equilibrium within the liposome toward the right, to production of protons.

B. Boronic Acid Compound

Figure 1B:
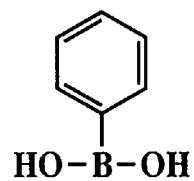
Figure 1C:
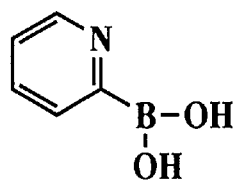
Figure 1D:
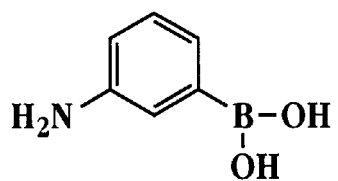
Figure 1E:
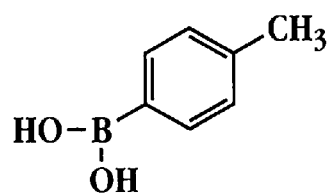

The preformed liposomes, described above, are incubated with the therapeutic compound to be encapsulated within the liposomes and a with boronic acid compound. A variety of boronic acid compounds are suitable for use in the present invention, and some representative boronic compounds are shown in FIGS. 1A–1E. FIG. 1A shows the generic form for a boronic acid compound and FIGS. 1B–1E show structures for exemplary boronic acid compounds, where FIG. 1B is phenylboronic acid, FIG. 1C is 2-pyridylboronic acid; FIG. 1D is 3-aminophenylboronic acid; and FIG. 1E is p-tolueneboronic acid. Other exemplary boronic acid compounds include 3,5-bis(trifluoromethyl) benzeneboronic acid, 4-carboxybenzeneboronic acid, 3-nitrobenzeneboronic acid, and 4-methylbenzeneboronic acid.

More generally, any boronic acid compound that serves to form a complex with the therapeutic compound to be loaded and which is able to cross the liposome lipid bilayer membrane more readily than the therapeutic compound alone, is suitable for use in the method of the invention. Where the liposomes are for in vivo use, it is also preferable that the boronic acid compound be pharmaceutically acceptable.

In the studies conducted in support of the invention, liposomes were loaded with a therapeutic compound in the presence of between 1–40 mM phenylboronic acid. It will be appreciated that the concentration of boronic acid compound can vary depending on the therapeutic compound, the liposome composition, the incubation conditions, and the boronic acid compound itself. Generally, a boronic acid concentration of between about 1–100 mM is suitable, however this may be higher in certain cases. A more preferred range is between about 2–50 mM boronic acid compound. The optimal concentration of boronic acid for a given set of circumstances can be readily determined experimentally by one of skill in the art.

C. Therapeutic Compounds

Therapeutic compounds suitable for use in the method of the invention include any therapeutic compound having two nearby hydroxyl groups. For example, in a preferred embodiment, compounds having a 1,3 or 1,2 cis diol arrangement are contemplated. More preferably, the compound is one which is not able to pass through the liposome lipid bilayer membrane at a rate sufficient for significant accumulation in the liposomes. Such compounds are generally lipophobic and unable to readily cross the lipid bilayer.

Exemplary diol-containing compounds include galactosamine, clindamycin, doxifluridine, idoxuridine, ribavirin, riboflavin, ribostamycin, spiramycin, fluorouridine, glucosamine, amikacin, arebekacin, kanamycin, paronomycin, tobramycin, vancomycin, ribostamycin and erythromycin.

Other therapeutic compounds which do not have two nearby hydroxyl groups, such as cisplatin, can form a transiently stable complex with a boronic acid compound and are also contemplated for use in the method of the invention. In general, the method of the invention is suitable for use with any lipophobic compound that when complexed with a boronic acid compound forms a lipophilic complex that is able to cross a liposome lipid bilayer more readily than the compound alone.

D. Loading Method

Liposomes formed as described above are used in the method of the invention for loading a diol-containing compound. In accordance with the invention, the compound is added to a suspension of liposomes and the suspension is incubated under conditions effective to allow passage of the compound from the external medium into the liposomes. Incubation conditions suitable for drug loading are those which (i) allow diffusion of the compound-boronic acid compound complex into the liposomes, and (ii) preferably lead to high drug loading concentration, e.g., 50–200 mM drug encapsulated. It will be appreciated that the incubation conditions, e.g., time and temperature, will vary according to the liposome composition and the therapeutic compound. In some cases, the liposome suspension is incubated with the compound and the boronic acid compound at a temperature above the phase transition temperature of the liposome lipids. Thus, for liposomes formed predominantly of saturated phospholipids, the loading temperature may be as high as 60° C. or more. The loading time is typically between 15–120 minutes, depending on permeability of the complex formed between the therapeutic compound and the boronic acid compound.

During the incubation period, the boronic acid compound serves as a shuttle to transport the drug into the liposome. The boronic acid and the drug associate, either by hydrogen bonding between respective hydroxyl groups or by a transient bond formation, to form a hydrophobic complex in the external bulk medium of the liposome suspension. The drug-boronic acid complex crosses the liposome bilayer and once inside the liposome, e.g. either inside the central compartment or in an aqueous space between lipid bilayer, the complex dissociates into the two initial species. The compound, being impermeable to the liposome lipid bilayer, remains entrapped in the liposomes. The boronic acid compound is able to traverse the lipid bilayer and can return to the liposome exterior to shuttle another drug molecule to the inside of the liposome. After loading is complete, the boronic acid compound can be removed from the external medium of the liposome suspension by dialysis or diafiltration. Similarly, if the drug to be loaded is not substantially depleted from the external medium, the liposome suspension may be treated, following drug loading, to remove non-encapsulated drug. Free drug can be removed, for example, by molecular sieve chromatography, dialysis, or centrifugation.

In some cases, the drug-boronic acid complex may be charged and not able to readily permeate the liposome lipid bilayer. In these cases, ad additional carrier ion can be added to facilitate loading of the drug. Such a carrier ion is one having a lipophilic portion and an appropriate charge to offset or balance the charge of the complex. Examples of carrier ions include trioctylmethylammonium and tetrabutylammonium ions.

In another embodiment of the invention, an ion gradient is used in conjunction with the boronic acid shuttle system. The use of an ion gradient results in a higher concentration of drug inside the liposomes. Several ion gradients, such as ammonium ion gradients or pH gradients can be used for therapeutic compounds containing ionizable amine groups.

In studies performed in support of the invention, galactosamine and glucosamine were loaded into liposomes using a boronic acid compound, phenylboronic acid, in conjunction with an ammonium ion gradient. A liposome suspension was prepared, as described in Example 1A, which included liposomes having a 250 mM ammonium sulfate solution in the liposome interior and a sucrose external bulk medium. The liposomes were incubated in the presence of the drug to be loaded, glucosamine or galactosamine at various concentration, and in the presence or absence (as a control) of phenylboronic acid, at various concentrations, as set forth in Example 1B.

Figure 2:
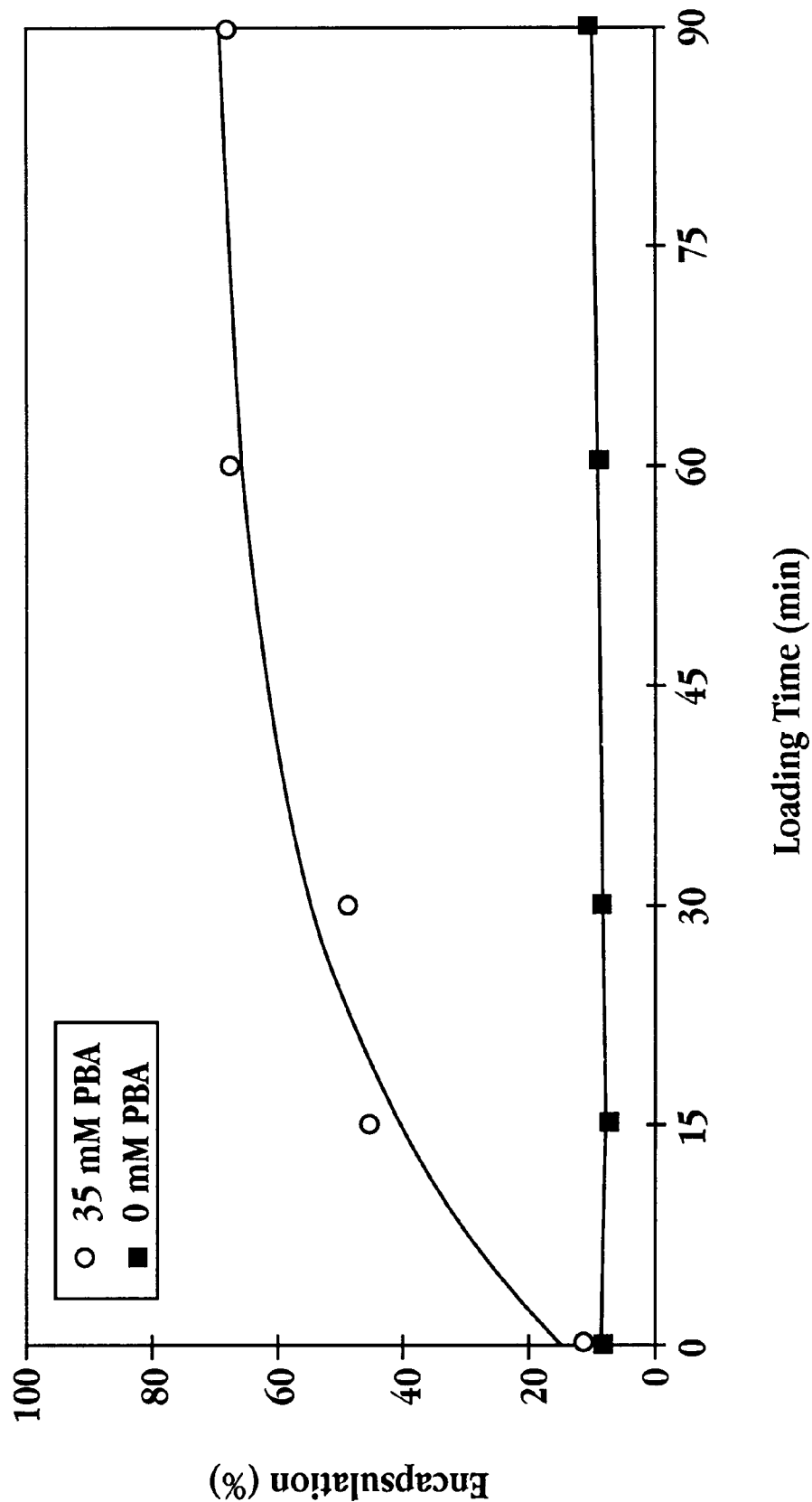
FIG. 2 is a plot showing the percentage of galactosamine encapsulation in liposomes as a function of time in minutes for preformed liposomes loaded with galactosamine in the presence of phenylboronic acid (open circles) and in the absence of phenylboronic acid (saline alone, closed squares)
Figure 3:
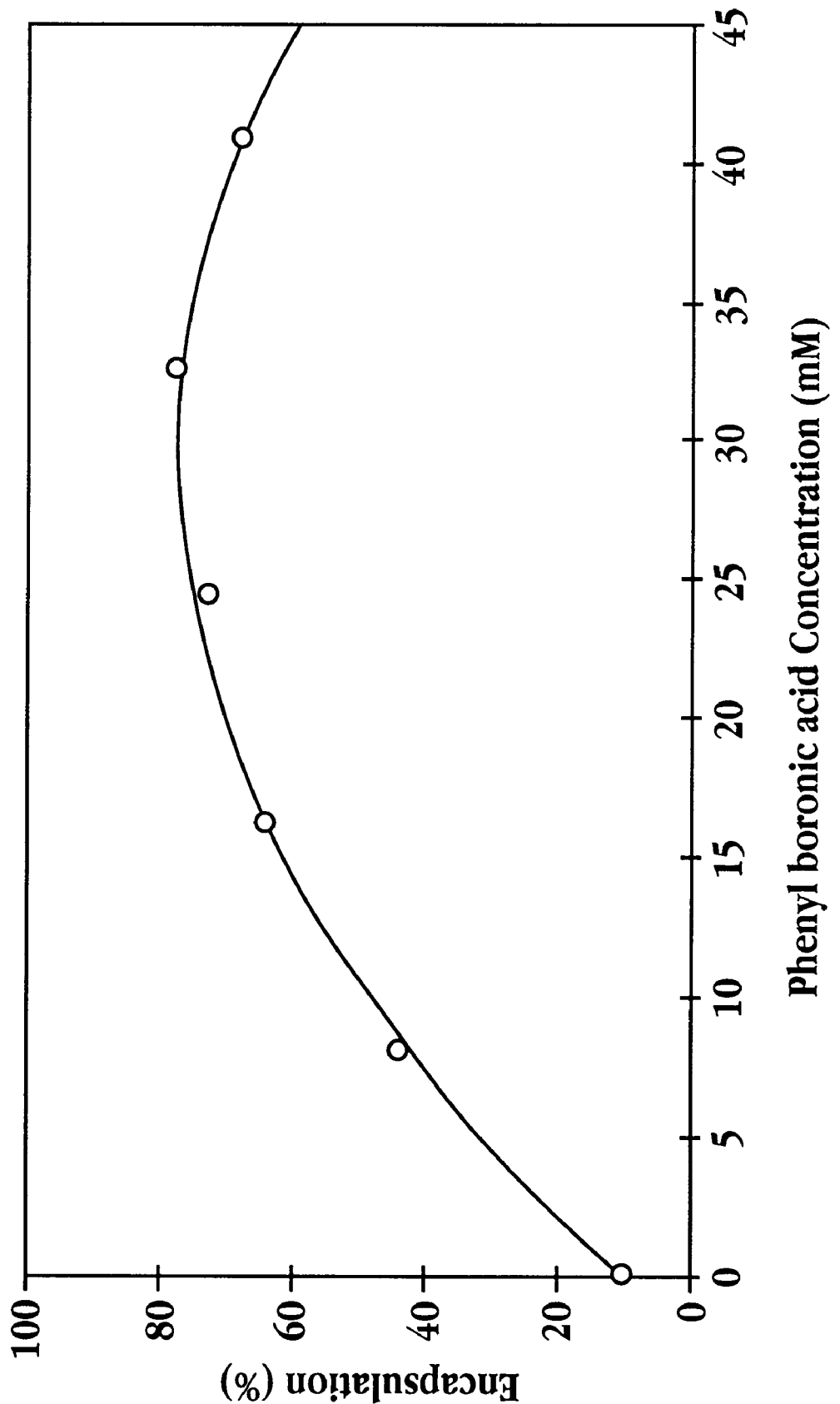
FIG. 3 shows the percentage of galactosamine encapsulated in liposomes as a function of phenylboronic acid concentration in mM.
Figure 4:
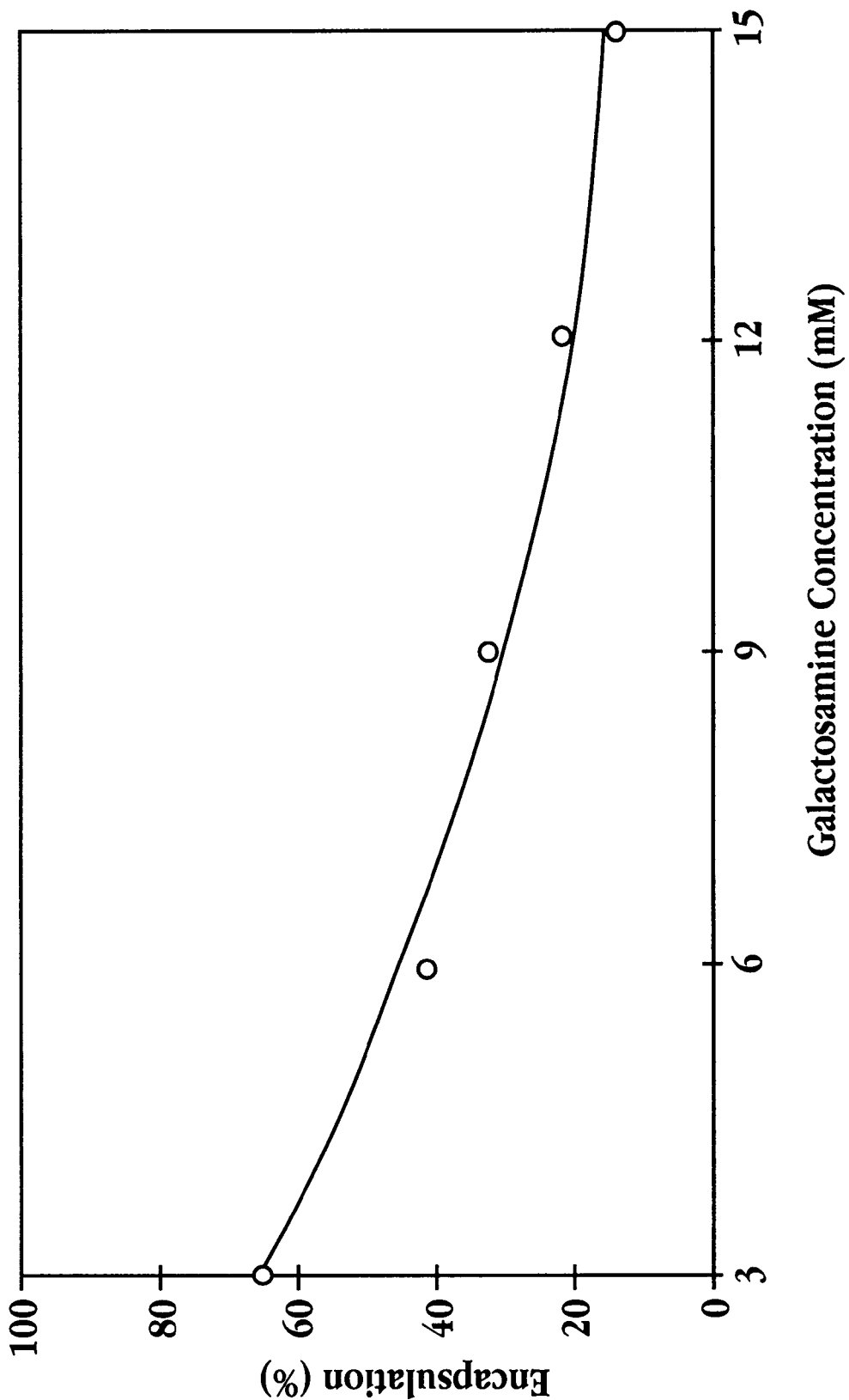
FIG. 4 shows the percentage of galactosamine encapsulated in liposomes as a function of galactosamine concentration in mM.

FIGS. 2–4 shows the results for loading galactosamine. FIG. 2 shows the amount of galactosamine entrapped in the liposomes as a function of loading time. Liposomes were loaded in the presence of 5 mM galactosamine and in the presence of 35 mM phenylboronic acid (open circles) or in the absence of phenylboronic acid (saline alone, closed squares). As seen in FIG. 2, the presence of the boronic acid significantly enhanced the loading, as measured by the percentage of drug encapsulated, into the liposomes. After one hour of loading time, a 7-fold increase in amount of encapsulated galactosamine was observed.

FIG. 3 shows the percentage of galactosamine encapsulated in liposomes as a function of phenylboronic acid concentration added to the incubation medium. As seen for this set of conditions, the maximum entrapment of galactosamine is achieved between about 25–40 mM phenylboronic acid. In this study the galactosamine concentration was at 5 mM, and it will be appreciated that as this concentration changes, the concentration of boronic acid compound to obtain optimal loading in a given time will change accordingly.

FIG. 4 shows the percentage of galactosamine encapsulated in liposomes as a function of galactosamine concentration in mM in the presence of 35 mM of phenylboronic acid.

Figure 5:
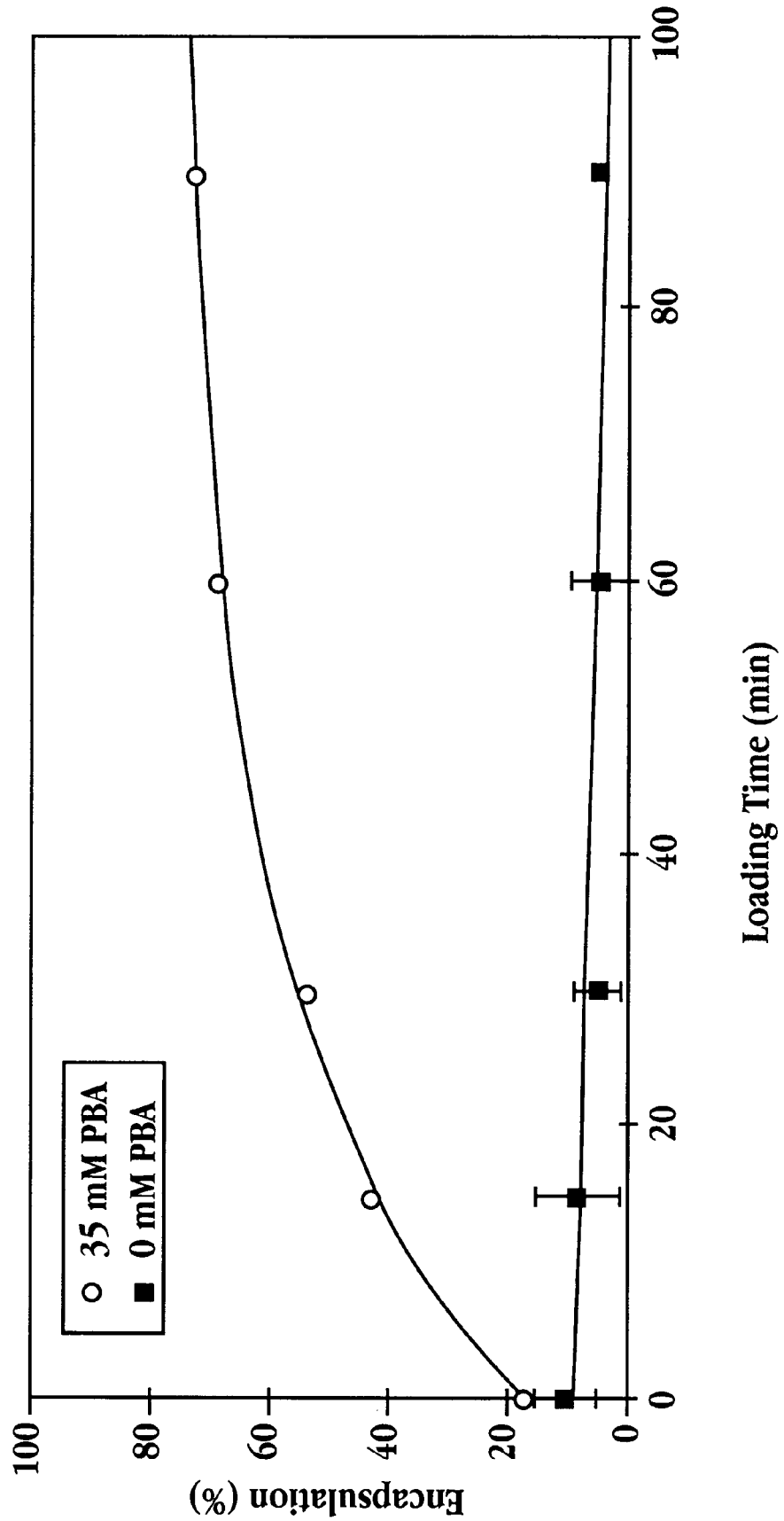
FIG. 5 is a plot showing the percentage of glucosamine encapsulation in liposomes as a function of time in minutes for preformed liposomes loaded with glucosamine in the presence of phenylboronic acid (open circles) and in the absence of phenylboronic acid (saline alone; closed squares)

In other studies performed in support of the invention, glucosamine was loaded into liposomes prepared as described in Example 1A. FIG. 5 shows the amount of glucosamine encapsulated in liposomes as a function of time in the presence of 15 mM phenylboronic acid (open circles) and in the absence of phenylboronic acid (saline alone; closed squares). As seen, the a significant enhancement in drug loading was achieved in the presence of phenylboronic acid, where as with galactosamine, nearly a 7-fold improvement in loading was achieved.

Figure 6:
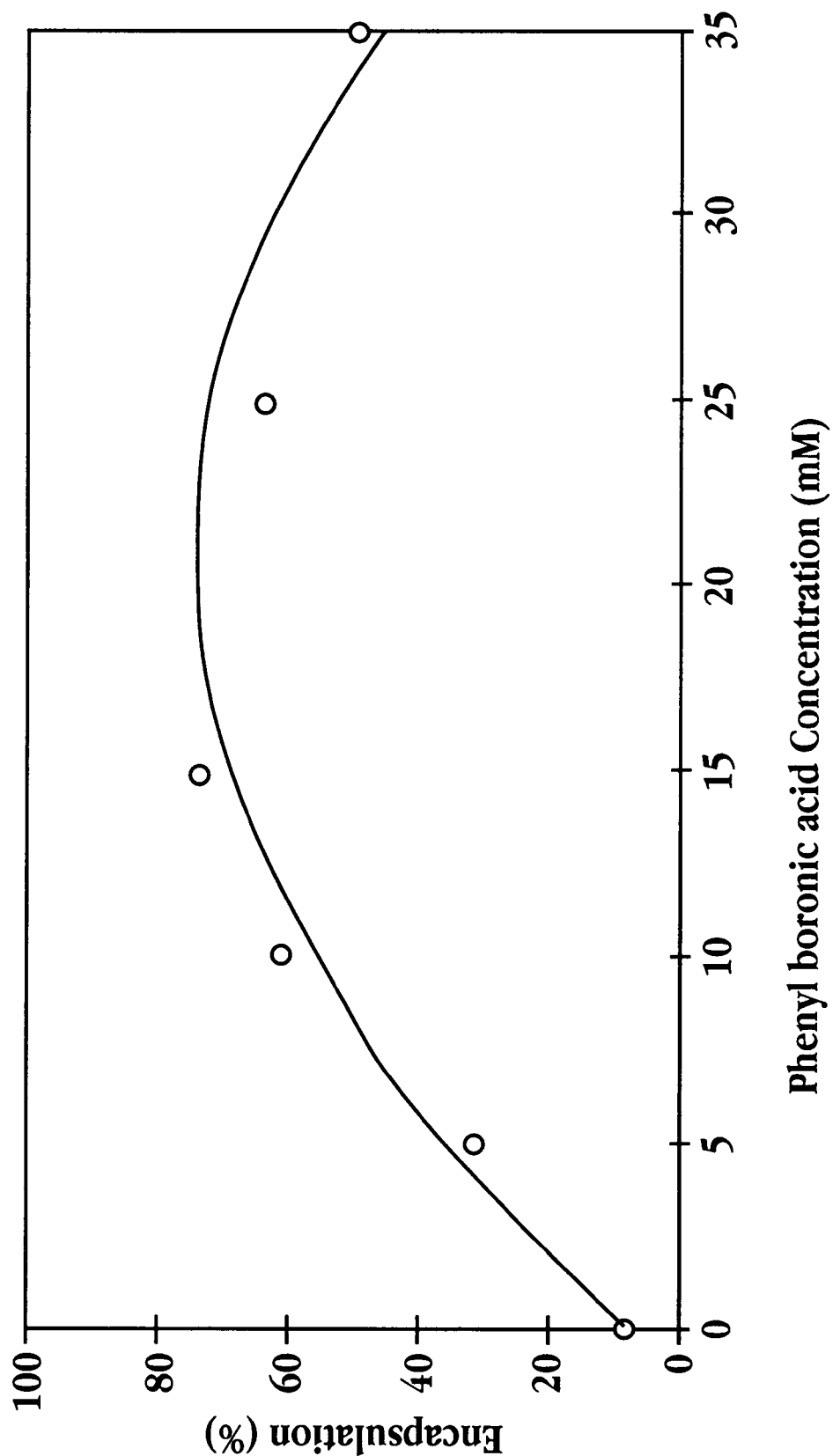
FIG. 6 shows the percentage of glucosamine encapsulated in liposomes as a function of phenylboronic acid concentration in mM.

FIG. 6 shows the percentage of glucosamine encapsulated in liposomes as a function of phenylboronic acid concentration in mM. In this study the galactosamine concentration was at 5 mM, and it will be appreciated that as this concentration changes, the concentration of boronic acid compound to obtain optimal loading in a given time will change accordingly.

II. Examples

The following example illustrates the method of the invention and is in no way intended to be limiting.

EXAMPLE 1

Liposome Loading Method

A. Liposome Preparation

A suspension of liposomes composed of 56.4 mole percent hydrogenated soy phosphatidylcholine (HSPC)(Avanti Polar Lipids, Birmingham, Ala.), 38.3 mole percent cholesterol (Sigma, St. Louis, Mo.), and 5.3 mole percent methoxypolyethyleneglcyol carbamate of distearoly phosphatidylethanolamine (mPEG-DSPE, prepared as described previously in Zalipsky, S., et al, *Bioconjugate Chem.*, 4:296–299 (1993)).

The liposome suspension was prepared by dissolving the lipids in ethanol and drying the lipids to a thin film. The lipid film was hydrated with an ammonium sulfate solution to form liposomes and then the liposomes were extruded to obtain liposomes of about 100 nm. The liposome suspension was dialyzed against a sucrose solution, thus obtaining liposomes encapsulating a 250 mM ammonium sulfate solution in an external buffer of 10% sucrose at pH 6.5. The total lipid concentration was 52 μmoles/ml.

B. Liposome Loading

After liposome formation, glucosamine or galactosamine at various concentrations were added to suspensions of liposomes in the presence of absence of phenylboronic acid, also at various concentrations. The suspensions were incubated for various times and temperatures, and at selected timepoints aliquots of the incubating suspensions were removed and assayed for liposomal encapsulation of glucosamine or galactosamine. The assay comprised mixing the aliquot with citrate-poly(methacrylic acid)-saline and incubating for 15 minutes to ensure complete liposome aggregation. The aliquots were then centrifuged at 464 g for 15 minutes. After removal of the supernatant, entrapped compound was released from the pellet by adding 2%. Triton X-100 saturated borate solution. Then picrylsulfonic acid was added to both the supernatant and dispersed pellet solutions and the tubes were incubated at room temperature for 30 minutes. Compound concentrations were determined by reading absorbance bat 478 nm. Loading efficiency, defined as the percentage of the compound associated with the pellet, was then calculated. The results are shown in FIGS. 2–6.

Although the invention has been described with respect to particular embodiments, it will be apparent to those skilled in the art that various changes and modifications can be made without departing from the invention.

It is claimed:

1. A method for loading a therapeutic compound having a cis diol moiety into liposomes, comprising adding to a suspension of liposomes (i) the compound to be loaded into the liposomes and (ii) a boronic acid compound; and by said adding, achieving accumulation of the compound within the liposomes.

2. The method of claim 1, wherein said adding includes adding a boronic acid compound selected from the group consisting of phenylboronic acid, 2-pyridylboronic acid, 3-aminophenylboronic acid, p-tolueneboronic acid, 3,5-bis(trifluoromethyl)benzeneboronic acid, 4-carboxybenzeneboronic acid, 3-nitrobenzene boronic acid and 4-methylbenzeneboronic acid.

3. The method of claim 1, wherein said adding includes adding between 2–50 mM of the boronic acid compound.

4. The method of claim 1, wherein said adding includes adding between 2–50 mM phenylboronic acid.

5. The method of claim 1, wherein said adding includes adding a compound having a 1,2 cis-diol moiety.

6. The method of claim 1, wherein said adding includes adding a compound having a 1,3 cis-diol moiety.

7. The method of claim 1, wherein said adding includes adding a glycoside compound.

8. The method of claim 1, wherein said adding includes adding a compound selected from the group consisting of galactosamine, ribavirin, idoxuriding, amikacin, tobramycin, and glucosamine.

9. The method of claim 1, wherein said adding includes adding to a suspension of liposomes having a surface coating of hydrophilic polymer chains.

10. A method for loading a therapeutic compound having a cis diol moiety into liposomes, comprising preparing a suspension of liposomes composed of a vesicle-forming lipid;

incubating the liposomes in the presence of (i) the compound to be loaded and (ii) a boronic acid compound;

by said incubating, achieving accumulation of the compound within the liposomes.

11. The method of claim 10, wherein said incubating includes incubating in the presence of a boronic acid compound selected from the group consisting of phenylboronic acid, 2-pyridylboronic acid, 3-aminophenylboronic acid, p-tolueneboronic acid, 3,5-bis(trifluoromethyl)benzeneboronic acid, 4-carboxybenzeneboronic acid, 3-nitrobenzene boronic acid and 4-methylbenzeneboronic acid.

12. The method of claim 11, wherein said incubating includes incubating in the presence of between 2–50 mM of the boronic acid compound.

13. The method of claim 10, wherein said incubating includes incubating in the presence of between 2–50 mM phenylboronic acid.

14. The method of claim 10, wherein the compound is a glycoside.

15. The method of claim 10, wherein the compound has a 1,2 cis-diol moiety.

16. The method of claim 10, wherein the compound has a 1,3 cis-diol moiety.

17. The method of claim 10, wherein the compound is selected from the group consisting of galactosamine, ribavirin, idoxuriding, amikacin, tobramycin, and glucosamine.

18. The method of claim 10, wherein said preparing includes preparing liposomes to have an inside/outside ion gradient.

19. The method of claim 10, wherein said preparing includes preparing liposomes to have an inside/outside ammonium ion gradient.

20. The method of claim 19, wherein said incubating includes incubating the liposomes in the presence of a compound having an ionizable amine.

21. The method of claim 10, which further includes the step of removing the boronic acid after said incubating.

* * * * *